United States Patent
Casara et al.

(10) Patent No.: US 8,293,201 B2
(45) Date of Patent: Oct. 23, 2012

(54) METHOD FOR THE RECOVERY OF AMMONIA FROM A GASEOUS STREAM IN A SYNTHESIS PROCESS OF UREA

(75) Inventors: Paolo Casara, Schio (IT); Alessandro Gianazza, Legnano (IT); Ivano Miracca, Milan (IT); Giuseppe Merelli, Vertova (IT); Gustavo Capannelli, Genoa (IT); Aldo Bottino, Genoa (IT)

(73) Assignee: Saipem S.p.A., San Donato Milanese (IT)

( * ) Notice: Subject to any disclaimer, the term of this patent is extended or adjusted under 35 U.S.C. 154(b) by 72 days.

(21) Appl. No.: 12/743,717

(22) PCT Filed: Nov. 14, 2008

(86) PCT No.: PCT/EP2008/009684
§ 371 (c)(1),
(2), (4) Date: Nov. 2, 2010

(87) PCT Pub. No.: WO2009/065534
PCT Pub. Date: May 28, 2009

(65) Prior Publication Data
US 2011/0091369 A1    Apr. 21, 2011

(30) Foreign Application Priority Data

Nov. 21, 2007    (IT) .............................. MI2007A2206

(51) Int. Cl.
*B01J 19/00* (2006.01)
*C01C 1/02* (2006.01)
(52) U.S. Cl. ......... 423/237; 423/238; 422/129; 422/187
(58) Field of Classification Search .................. 423/237, 423/238; 422/129, 187
See application file for complete search history.

(56) References Cited

U.S. PATENT DOCUMENTS

| | | | |
|---|---|---|---|
| 5,645,703 A | | 7/1997 | Tsai |
| 7,485,275 B2 * | | 2/2009 | Asprion et al. ............... 423/220 |

FOREIGN PATENT DOCUMENTS

| | | |
|---|---|---|
| EP | 1 695 755 | 8/2006 |
| GB | 2 383 034 | 6/2003 |

OTHER PUBLICATIONS

U.S. Appl. No. 13/143,988, filed Jul. 11, 2011, Casara, et al.
U.S. Appl. No. 13/387,836, filed Jan. 30, 2012, Casara.

* cited by examiner

*Primary Examiner* — Timothy Vanoy
(74) *Attorney, Agent, or Firm* — Oblon, Spivak, McClelland, Maier & Neustadt, L.L.P.

(57) ABSTRACT

A process for the recovery of ammonia contained in a gaseous purging stream produced in a synthesis process of urea.

30 Claims, 1 Drawing Sheet

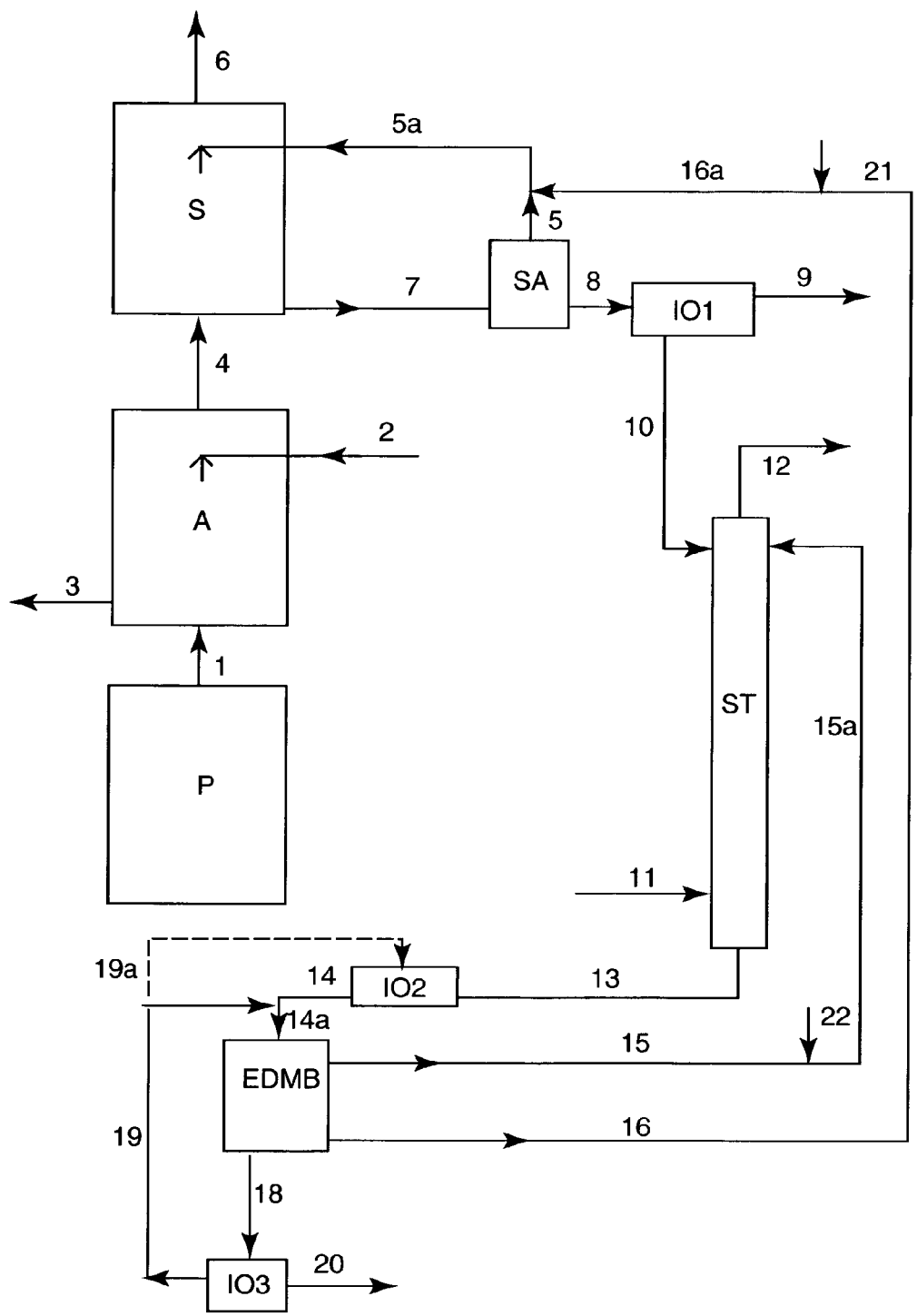

METHOD FOR THE RECOVERY OF AMMONIA FROM A GASEOUS STREAM IN A SYNTHESIS PROCESS OF UREA

This application is a 371 of PCT/EP08/09684 filed Nov. 14, 2008.

The present invention relates to a method for the recovery of ammonia from a gaseous stream in a urea synthesis process.

The synthesis of urea is effected by the reaction of ammonia and carbon dioxide at high pressure and temperature, the subsequent separation of the urea from the mixture containing the non-reacted products and recycling of the same to the reactor.

All industrial processes for the preparation of urea are therefore based on direct synthesis according to the following reaction:

$$2NH_3 + CO_2 \leftrightarrow CO(NH_2)_2 + H_2O \quad (A)$$

This synthesis takes place in two distinct reaction steps:

$$NH_3 + CO_2 \leftrightarrow (NH_2)COONH_4 \quad (A')$$

$$(NH_2)COONH_4 \leftrightarrow CO(NH_2)_2 + H_2O \quad (A'')$$

In the first step (A') an exothermic equilibrium reaction takes place having a high reaction rate at room temperature, which, at the high temperatures required by step (A''), requires high pressures to reach a favourable equilibrium.

In the second step (A'') an endothermic reaction takes place, which only reaches a significant rate at high temperatures (>150° C.), with an equilibrium state which, at 185° C., starting from a mixture of reagents in a stoichiometric ratio, leads to a $CO_2$ conversion slightly higher than about 50%. This unsatisfactory conversion can be conveniently increased by raising the $NH_3/CO_2$ ratio.

The above two reaction steps do not normally take place in separate zones of the reactor, but contemporaneously in the reaction mixture, which therefore contains urea, water, ammonia, carbon dioxide and ammonium carbamate with a relative concentration, in the different points of the reactor, depending on the different thermodynamic and kinetic factors which contribute to the process.

Processes for the production of urea by direct synthesis starting from ammonia and carbon dioxide have been widely illustrated and described in the specific literature of the field. A large review of the most common processes for the production of urea can be found, for example, in "Encyclopedia of Chemical Technology" Ed. Kirk-Othmer, Wiley Interscience, fourth ed. (1998), Supplement, pages 597-621.

Industrial processes for the production of urea normally carry out the synthesis in a reactor fed with $NH_3$, $CO_2$ and with the aqueous solutions of ammonium carbonate and/or carbamate coming from the recycled streams of the non-converted reagents, at temperatures ranging from 150 to 215° C., at pressures of at least 130 atm, with a $NH_3/CO_2$ molar ratio of between 2.5 and 5, calculated with respect to the sum of the feeding streams, including ammonia in the form of ammonium salt. In addition to the water formed and excess $NH_3$ fed, the reactor eluent still contains considerable quantities of $CO_2$, mainly in the form of non-converted ammonium carbamate.

The molten urea is solidified in the final section of the plant, into a granular form, in suitable granulators or prilling towers, by means of cooling with air.

Many of the environmental problems associated with urea production plants are caused by the above-mentioned granulation or prilling sections.

The processes which take place in this section, in fact, currently envisage the emission into the atmosphere of large quantities of air contaminated by ammonia (about 50-250 mg/$Nm^3$ air), urea (about 20-200 mg/$Nm^3$ air) and traces of formaldehyde.

Recent regulations, approved by numerous countries, have significantly lowered the maximum value allowed for the emission of these substances below these levels.

The abatement process of ammonia contained in a gaseous stream, by means of an acidic washing, for example using nitric acid, is a treatment that is well-known in literature, for example in U.S. Pat. No. 4,424,072. The treatment of the gaseous stream containing ammonia with an acidic aqueous solution leads to the production of an ammonium salt in aqueous solution.

In particular, when the gaseous stream containing ammonia which is subjected to acidic washing, is a gaseous stream coming from the final prilling or granulation section of a urea synthesis process, the aqueous solution containing the ammonium salt also contains urea and traces of formaldehyde.

The aqueous solution containing the ammonium salt cannot be recycled as such to the synthesis and/or concentration sections of urea, as the latter could then be contaminated by ammonium salts, which are absolutely undesirable for the purposes of certain subsequent uses of urea, for example for the synthesis of melamine.

Furthermore, the ammonium salt thus obtained would have such specifications as to make it unusable, as it is not at all suitable for the purposes of market interest.

The treatment of the aqueous solution is known from EP 1,695,755, comprising the ammonium salt with a membrane electrolytic process (MEP). This treatment allows the recovery of the acid used for the removal of ammonia, avoiding the recycling of the aqueous solution containing the ammonium salt to the urea plant and thus overcoming possible contamination problems.

MEP means a Membrane Electrolytic or Electrochemical Process, i.e. a process wherein two or more conductive solutions, separated by suitable semi-permeable membranes, are subjected to an electric field between an anode and a cathode: in this way it is possible to separate the cations from the ions present in the solution. The membranes can be anionic or cationic membranes, possibly combined with bipolar membranes. When bipolar membranes can be used, they enhance the energy efficiency of the process and consist of an anionic and a cationic membrane laminated together.

The solution suggested by EP 1,695,755 envisages the treatment of the aqueous solution comprising the ammonium salt with a membrane electrolytic process (MEP) which allows the recovery of the acid used for washing the ammonia present in the gaseous stream, which can be suitably recycled. An aqueous solution of ammonium hydroxide is also obtained, which can be thermally treated to obtain an gaseous ammonia stream which can be recycled to the urea synthesis plant.

The solution suggested in EP 1,695,755 has various drawbacks, in particular the production of ammonia from the electrodialysis cell in the form of a diluted solution of ammonium hydroxide, which requires specific and expensive thermal stripping treatment before being recycled in a sufficiently pure form to the urea synthesis plant.

Furthermore, the treatment of the aqueous solution comprising the ammonium salt with a membrane electrolytic process (MEP), as described in EP 1,695,755, can also allow the passage of undesired ions which lead to an aqueous solution of ammonium hydroxide which is not completely recyclable, or to a decrease in the process efficacy due to the undesired back-migration of neutral $NH_3$ through the membrane.

The Applicant has now found a process which overcomes the above-mentioned drawbacks of the state of the art and further enhances the recovery process of ammonia in a urea synthesis process.

BRIEF DESCRIPTION OF THE FIGURE

The FIGURE schematically represents the treatment steps of a gaseous purging stream leaving the prilling or granulation section of a urea synthesis process.

An object of the present invention therefore relates to a process for the recovery of ammonia contained in a purging gaseous stream, obtained in a synthesis process of urea, said process comprising the following phases:

a) subjecting the gaseous purging stream to a washing with an aqueous acidic solution, at a pH ranging from 1 to 6, with the formation of a first purified gaseous stream and an aqueous solution containing an ammonium salt;

b) subjecting the aqueous solution containing the ammonium salt coming from phase a) to stripping, after treatment with a strong base, at a temperature ranging from 50 to 250° C. and a pressure ranging from 1 to 40 absolute bar, with the formation of a second gaseous stream comprising $NH_3$, $H_2O$ and possibly $CO_2$ and a solution containing a salt of the cation of said strong base;

c) subjecting the solution containing the salt of the cation of the strong base coming from phase b) to a Membrane Electrochemical Process (MEP) with the formation of an aqueous solution of the acid used in phase a), an aqueous solution of the base used in phase b) and possibly a diluted aqueous solution of the cation salt of the strong base;

d) recycling said aqueous solution of the acid and aqueous solution of the base to phase a) and to phase b) respectively, and recycling said second gaseous stream coming from phase b) to the urea synthesis process.

An object of the present invention also relates to equipment for effecting the above process is, comprising:

an acidic washing unit (scrubber) in which a gaseous purging stream containing ammonia is put in contact with an acid, a stripping unit (stripper) of ammonia, in which an aqueous stream of an ammonium salt is put in contact with a strong base and the free ammonia thus produced is extracted as vapour from the aqueous stream, and a Bipolar Membrane Electrodialysis (BMED) or Electrodialysis (ED) unit in which a stream containing the acid, a stream containing the base and possibly a stream containing a dilute solution of the corresponding salt, are formed.

When in phase c), there is the formation of a diluted aqueous solution of the cation salt of the strong base, in the subsequent phase d) this solution is concentrated and recycled to the feeding of phase c).

The gaseous purging stream treated according to the process of the present invention can derive from various sections and equipment of the urea synthesis process. In the preferred and most relevant case, as a result of the gas volumes normally involved, it comes from the urea solidification section which, as is well-known, represents the area of the synthesis plant in which the urea, molten or in a concentrated solution, is cooled and solidified into a generally granular form, suitable for delivery and use in agriculture. Different solidification technologies are possible, the most common and preferred, as described before, being known as granulation and prilling, which use, as cooling agent, a gaseous stream in large volumes.

There are, however, also other sources of gaseous purging or vent gaseous streams containing ammonia as polluting agent in urea plants, which cannot be released without an adequate recovery treatment, such as the streams in the aspiration ducts situated in different areas of the facility, in the storage areas, or the streams for purging the inert products. All these streams can be treated according to the present invention, obtaining the double advantage of an improvement in the environmental impact and a further recovery of ammonia to be recycled to the plant.

The gaseous purging stream coming from the synthesis process of urea consequently generally consists of a gas contaminated by ammonia (about 50÷250 $mg/Nm^3$ gas), urea (about 20÷200 $mg/Nm^3$ gas), plus traces of formaldehyde.

This gas normally consists of air, but processes which use an inert gas different from air are not excluded from the scope of the present invention; in these cases, said gaseous purging stream mainly consists of said inert gas.

The gaseous purging stream preferably comes from the urea synthesis plant at a temperature of about 45-100° C. and is subjected to a preliminary washing with water to eliminate most of the urea and formaldehyde present.

The gaseous purging stream which is subjected to phase a) of the process according to the present invention, still contains, however, urea and traces of formaldehyde. The urea hydrolyzes, by means of the treatment of the subsequent phase b), to give $CO_2$ and $NH_3$; this represents a particular advantage with respect to the processes of the state of the art, as the presence of urea in the salt solution, which is obtained from the stripper, can create numerous problems in the subsequent EDMB or ED treatment of the salt solution. Furthermore, in this way, it is possible to also recover the further ammonia contained in the urea, avoiding further dispersion into the environment.

Phase a) is preferably carried out with an acidic aqueous solution of any strong acid of the protic type, preferably $HNO_3$, $H_2SO_4$, $H_3PO_4$, more preferably $HNO_3$.

Phase a) is preferably effected at a pH ranging from 4 to 5.5.

The aqueous solution containing the ammonium salt coming from phase a) also contains urea and traces of formaldehyde.

The aqueous solution containing the ammonium salt coming from phase a) preferably envisages a concentration of ammonium salt ranging from 5 to 50% by weight, preferably from 8 to 25% by weight.

It can be possibly concentrated by means of an reverse osmosis process, before being subjected to phase b) of the process according to the present invention.

Reverse osmosis is a process (known in literature) wherein a saline aqueous solution is concentrated thanks to the use of a suitable semi-permeable membrane. The saline solution pressed against a semi-permeable membrane (at a pressure higher than the osmotic pressure of the saline solution to be treated); said membrane is substantially only permeable to water and allows a stream of saline concentrated solution and a stream of water without, or substantially without salts, to be obtained.

The aqueous solution containing the ammonium salt coming from phase a) and subjected to reverse osmosis has a concentration of ammonium salt ranging from 6 to 66% by weight, preferably from 10 to 30% by weight.

The gaseous stream which is formed in phase a) of the process according to the present invention consists of substantially pure air or another inert gas (for example nitrogen): in fact, it has an ammonia content ranging from 10 to 25 mg/Nm³ gas and a urea content ranging from 5 to 30 mg/Nm³ gas. If the purified gaseous stream consists of air or nitrogen, it can be released into the atmosphere without further treatment as it is conformant with the environmental regulations in force.

The aqueous solution containing the ammonium salt coming from phase a), possibly concentrated as mentioned above, is then subjected to treatment with a strong base, at a temperature ranging from 50 to 250° C. and a pressure ranging from 1 to 40 absolute bar, with the formation of a solution comprising a salt of the cation of said strong base and a gaseous stream comprising $NH_3$, $H_2O$ and possibly $CO_2$.

In particular, phase b) comprises the shifting of ammonia from the ammonium salt, as a result of the addition of an aqueous solution of a strong base.

The strong base is preferably an ionic hydroxide having a high solubility in water, for example NaOH or KOH. More preferably the strong base is NaOH.

In the non-limiting case in which $HNO_3$ is used in phase a) and NaOH in phase b), the following reaction occurs:

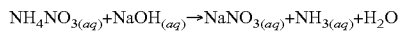

$$NH_4NO_{3(aq)} + NaOH_{(aq)} \rightarrow NaNO_{3(aq)} + NH_{3(aq)} + H_2O$$

The aqueous solution of the strong base is added in such a quantity that it neutralizes the ammonium salt solution from the excess acid and substantially shifts all the ammonia.

When the strong base used in phase b) is NaOH, for example, the salt is a sodium salt, in particular the salt is sodium nitrate, when the acid used in phase a) is $HNO_3$.

The free ammonia shifted from the ammonium salt, present in the aqueous solution as hydrated ammonia or ammonium hydroxide, migrates in the gas phase according to the phase equilibrium under the pressure and temperature conditions of the process and is separated as a gaseous stream.

In phase b), a second gaseous stream comprising $NH_3$, $H_2O$ and possibly $CO_2$, as mentioned, is formed, which can be recycled to the urea synthesis process or to an ammonia production process, preferably after concentration and possible partial or total condensation.

Phase b) consequently allows anhydrous ammonia to be obtained, or in aqueous solution in any proportion, which can be recycled to the urea synthesis process or to other processes such as synthesis processes of ammonia.

In phase b), ammonia is extracted from the aqueous solution containing the salt of the strong base (stripping).

Phase b) is preferably effected by adding steam to favour reaching the desired temperature and to favour the removal of ammonia. Alternatively, the heat can be supplied by means of indirect heating. The steam formed by thermal effect or fed from the outside, advantageously also produces a driving effect of ammonia to the gaseous phase, favouring its extraction from the solution, according to the known principles of the stripping technique.

The temperature and pressure conditions in phase b) must be selected so as to lead to the formation of the solution and gaseous stream.

Phase b) is preferably carried out at a temperature ranging from 140 to 200° C. and pressure ranging from 3 to 18 absolute bar.

In a preferred embodiment, by operating during the stripping phase at about 3 bar and a temperature of about 150° C., the stream comprising $NH_3$, $H_2O$ and $CO_2$ has a concentration of ammonia which varies from 15 to 25% by weight.

In phase c) of the process according to the present invention the aqueous solution containing the salt of the cation of the strong base used in phase b) is subjected to a Membrane Electrochemical Process (MEP) with the formation of an aqueous solution of the acid used in phase a), an aqueous solution of the base used in phase b) and possibly a diluted aqueous solution of the salt of the cation in the strong base used in phase b).

The aqueous solution containing the salt of the cation of the strong base used in phase b) can be previously concentrated by means of reverse osmosis.

The aqueous solution containing the cation salt of the strong base used in phase b), obtained as a result of the shift of ammonia, is substantially subjected to an electrochemical regeneration in accordance with phase c).

As already mentioned, a Membrane Electrochemical Process MEP is a process wherein two or more conductive solutions separated by one or more suitable semi-permeable membranes are subjected to an electric field between an anode and a cathode; in this way, it is possible to separate the cations from the anions present in the solution. The membranes can be anionic or cationic, possibly combined with bi-polar membranes. When bi-polar membranes can be used, they allow the process energy efficiency to be increased and consist of an anionic membrane and a cationic membrane laminated together. Bipolar Membrane Electrodialysis (EDMB) differs from Electrodialysis (ED) specifically in the use of bipolar membranes.

A more general discussion of the theoretical aspects and practical production of electrolytic membrane cells can be found, for example, in the chapter "Electrodialysis" in the already mentioned publication: "Encyclopedia of Chemical Technology" Ed. Kirk-Othmer, Wiley Interscience, 4$^{th}$ edition (1998), Vol. 9, pages 343-356.

Said solution can be previously concentrated by means of reverse osmosis and subsequently sent to the EDMB or ED cell.

The EDMB or ED cell gives the following products: an aqueous solution of the acid used in phase a), preferably with a normal concentration ranging from 0.1N and 5N, an aqueous solution of the base used in phase b), preferably with a normal concentration ranging from 0.1N to 5N, and possibly a diluted aqueous solution of the salt of the cation of the strong base used in phase b). More preferably, the solutions of acid and base obtained by MEP in phase c) have concentrations ranging from 0.5N to 2.5N, independently.

The acid aqueous solution can be used for the absorption of further ammonia from the starting gaseous stream in phase a) of the process according to the present invention, i.e. it is recycled to the so-called acid scrubber phase, after possible addition of the necessary quantity of water and acid necessary for maintaining the desired concentration (make-up acid).

The diluted aqueous solution of the salt can be concentrated, for example, by distillation or by means of reverse osmosis and recycled to the feeding to phase c) of the process according the present invention.

In particular, in a preferred embodiment which comprises the use of nitric acid in phase a) and NaOH in phase b), the aqueous solution of $NaNO_3$ coming from phase b), with a concentration of $NaNO_3$ varying from 1 to 30% by weight, is sent to the EDMB or ED cell.

In an embodiment, the EDMB or ED cell gives the following products:

NaOH (aq) (about 0.5-20%, preferably 3-10% by weight) is recycled to the stripping phase, after the possible addition of the necessary quantity of water and make-up acid;

HNO₃ (aq) (about 1-30%, preferably 3-18% by weight) which is recycled to the so-called acid scrubber phase, after the possible addition of the necessary quantity of water and make-up acid;

a diluted aqueous solution of NaNO₃ which is concentrated, preferably by means of reverse osmosis, with the formation of H₂O and a NaNO₃ (aq) solution to be recycled to the feeding to phase c) of the process according to the present invention.

The improved process according to the present invention thus allows the recovery of polluting products such as ammonia and urea, contained in a gaseous purging stream, in a plant for the production of urea, advantageously allowing concentrated ammonia solutions to be obtained. These solutions therefore do not require specific thermal treatment before being recycled to the urea synthesis plant. The process therefore has a high energy efficiency.

Furthermore, the process according to the present invention has the advantage of not being bound to the selectivity of the membrane(s) as substantially all the ammonia is removed with the second gaseous stream which is formed in phase b) of the process. In this way the efficiency of the acid solution regeneration is greatly improved with respect to the direct processing of the ammonium salt. The energy consumption of the ED or EDMB section in a typical embodiment of the present invention wherein sodium nitrate is formed in phase b), can be as low as about 350 KJ/mol$_{NH3}$, and usually ranges from 350 to 600 KJ/mol$_{NH3}$, depending on the desired space velocity of the NaNO₃ solution.

A further advantage of the process according to the present invention also lies in the possibility of substantially eliminating all the urea present: in phase b), in fact, the temperature and pressure conditions cause an almost complete hydrolysis of the urea.

The process according to the present invention is further illustrated by means of the enclosed FIGURE, which schematically represents the treatment steps of the gaseous purging stream leaving the prilling or granulation section of a urea synthesis process, which represents a preferred embodiment of the process according to the present invention.

The functional details, such as pumps, valves and other items of equipment not significant for a full understanding of the schematized processes, are not shown in the above-mentioned FIGURE. The process, object of the present invention, should in no case be considered as being limited to what is described in the enclosed FIGURE, which has a purely illustrative purpose.

Furthermore, in order to simplify the present description, the term "liquid" is used indifferently with reference to streams of mixtures consisting of a single liquid phase or a mixed liquid-vapour phase. The term "gaseous" is used for streams or mixtures in which the liquid phase is substantially absent.

The scheme shown in the FIGURE illustrates a urea plant prilling or granulation section P, producing a gaseous stream containing impurities of ammonia and urea, connected through line 1 to a water washing section A. This section A comprises a water inlet line 2, an outlet line 3, and is connected, through line 4, to the acid scrubber section S. The acid scrubber section S comprises an inlet line 5a, an air (or other gas) outlet line 6 and is, in turn, connected to a buffer tank SA, through line 7. The buffer tank SA is connected, through lines 5 and 5a, to the acid scrubber S and to a first concentration section by reverse osmosis I01, through line 8. This section I01 comprises a water outlet line 9, and is connected to the stripping section ST through line 10.

The stripping section ST comprises a steam inlet line 11, a strong base inlet line 15a and an outlet line 12 of the gaseous stream containing ammonia, water and possibly CO₂ and is connected, through line 13, to a second concentration section by reverse osmosis I02. This section I02 is connected through lines 14 and 14a to the electrochemical regeneration section EDMB. The EDMB section is connected, through lines 15 and 15a, to the stripping section ST, through lines 16, 16a and 5a to the acid scrubbing section S and, through line 18 to a third concentration section by reverse osmosis I03. This section I03 is connected through lines 19 and 14a to the EDMB section and comprises a water outlet line 20.

With reference to the FIGURE, some possible embodiments of the process of the present invention are described hereunder, even if this description does not limit the overall scope of the invention itself.

The gaseous purging stream coming through line 1 from the prilling or granulation section P, consists of air contaminated by ammonia (about 50-250 mg/Nm³ air), urea (about 40-200 mg/Nm³ air in forced draft equipments, 20-100 mg/Nm³ air in natural draft ones) and traces of formaldehyde. This stream is sent to a water washing section A. This section A has two feeding streams, a stream consisting of water, which is fed through line 2 and a gaseous purging stream coming from the section P, through line 1. The gaseous stream at the outlet of the water washing section A, through line 4, consists of air, ammonia, urea and traces of formaldehyde. Part of the urea present in the initial gaseous stream has therefore been eliminated by the water washing and can be found in the aqueous solution at the outlet through line 3. This is preferably sent to the vacuum concentration section (not shown in the FIGURE) of the urea synthesis plant, for the recovery of the latter.

The gaseous stream at the outlet of the water washing section A, through line 4, is sent to the acid scrubber section S, where it is subjected to a washing with an acid aqueous solution of HNO₃ at a pH of about 5, with the formation of a gaseous stream substantially comprising pure air which is released into the atmosphere, through line 6 and an aqueous solution containing ammonium nitrate which, through line 7, is fed to a buffer tank SA.

The water washing section A can also be absent and in this case the gaseous purging stream 1 coming from section P is sent directly to the acid scrubber section S.

The buffer tank SA, when present, works as a reservoir of the acid aqueous solution to be recycled through line 5 and 5a to the acid scrubber section S. The solution of nitric acid leaving the buffer tank SA through line 5 is enriched by the aqueous solution of nitric acid coming from the EDMB section, through lines 16 and 16a, after possible dilution with water, if necessary, through line 21. The streams 5 and 16a, thus joined, are recycled through line 5a to the acid scrubber S.

A part of the aqueous solution of ammonium nitrate from the receiver SA, corresponding to the mass balance of the scrubbed ammonia, is sent, through line 8, to a first concentration section by reverse osmosis I01.

This section I01 concentrates the solution of ammonium nitrate and the concentrated solution thus obtained is then sent, through line 10, to the stripping section ST.

The section I01 can be absent and in this case the ammonium nitrate solution coming through line 8 of the buffer tank SA, is sent directly to the stripping section ST.

A stream of NaOH through line 15a, possibly a stream of steam through line 11 and the solution of ammonium nitrate through line 10, are fed to the stripping section ST.

The aqueous solution containing ammonium nitrate is treated with NaOH at a temperature ranging from 50 to 250° C. and a pressure ranging from 1 to 40 absolute bar, with the formation of a gaseous stream comprising $NH_3$, $H_2O$ and $CO_2$ which is removed through the outlet line 12 and can be recycled to the synthesis process of ammonia.

The solution of sodium nitrate formed after the stripping of ammonia, is sent, through line 13, to the second concentration section by reverse osmosis I02.

This section I02 concentrates the sodium nitrate and the concentrated solution thus obtained is then sent through lines 14 and 14a to the electrochemical regeneration section EDMB.

The section I02 can be absent and in this case the solution of sodium nitrate coming through line 13 from the stripping section ST, is sent directly to the EDMB section.

In the EDMB electrochemical regeneration section, the cell returns the following regeneration products and more specifically an aqueous solution of NaOH, an aqueous solution of nitric acid and a diluted aqueous solution of sodium nitrate.

The aqueous solution of NaOH has a concentration which preferably ranges from 3 to 10% by weight and, through lines 15 and 15a, is recycled to the stripping section ST. If necessary, this solution can be diluted by the addition of the necessary quantity of water through line 22.

The aqueous solution of $HNO_3$ has a concentration which preferably ranges from 3 to 18% by weight and, through lines 16, 16a and 5a, is recycled to the acid scrubber S. If necessary, this solution can also be diluted by the addition of the necessary quantity of water through line 21.

The diluted aqueous solution of sodium nitrate is sent to the third concentration section by reverse osmosis I03, through line 18.

The solution of sodium nitrate, leaving the concentration section I03, is recycled through lines 19 and 14a to the EDMB section, or, possibly, upstream, through line 19a, to the section IO2 for further concentration.

According to an alternative embodiment, not shown in the FIGURE, the sodium nitrate solution leaving the EDMB section is concentrated by feeding it directly to section IO2, together with the sodium nitrate solution from the stripping section ST.

EXAMPLE

A process according to the present invention was carried out in a plant as schematically represented in the FIGURE, that was connected to a 600 tonne/day urea production plant.

From the prilling section P, an air stream of 300,000 Nm3/h containing 28 Kg/h of ammonia and 55 Kg/h of urea, is sent, directly through line 4, to the acid scrubber section S, without any preliminary water washing. In section S the gas stream is scrubbed with 532,568 Kg/h of an acid aqueous solution at a pH of about 5, fed through line 5a, having the following composition:

| | |
|---|---|
| Water | 365.862 Kg/h |
| HNO₃ | 95 Kg/h |
| NH4NO3 | 119.436 Kg/h |
| Urea | 47.175 Kg/h | and resulting from the addition of 1,494 Kg/h of make-up water and 963 Kg/h of a 9.76% b.w. aqueous solution of nitric acid (through line 16a), to the recycle solution of line 5 from the buffer tank SA.

Through line 6, a substantially pure air stream is released from the scrubber S into the atmosphere, which only contains 9.4 mg/Nm³ of ammonia (3 Kg/h) and 27 mg/Nm³ of urea (8 Kg/h), and 2000 Kg/h of water.

An aqueous solution enriched in ammonium nitrate exits the scrubber S through line 7 and is fed to the buffer tank SA, to be recycled for the great part. A portion of this ammonium nitrate solution, consisting of 363 Kg/h of water, 119 Kg/h of $NH_4NO_3$, 47 Kg/h of urea and traces of nitric acid, is sent, without any concentration, to the stripping section ST, through lines 8 and 10, wherein it is added of a solution of 60 Kg/h NaOH in 869 Kg/h of water, coming from the EDMB section through line 15 and 15a, to bring the pH to about 11, and then heated up to about 160° C. in order to hydrolyze urea and release an ammonia gaseous stream through line 12, consisting of:

| | |
|---|---|
| Steam | 185 Kg/h |
| Ammonia | 51.6 Kg/h |
| CO₂ | 34.5 Kg/h |

A solution stream of sodium nitrate formed after the stripping of ammonia, containing 1048 Kg/h of water and 127 Kg/h $NaNO_3$, is sent through line 13, to the concentration section by reverse osmosis I02, wherein it is admixed with a preconcentrated recycle solution coming, through line 19 and 19a, from the reverse osmosis concentration unit IO3, containing 765 Kg/h of water and 85 Kg/h of $NaNO_3$. The resulting solution is concentrated by removing 453 Kg/h of water (25% concentration ratio). 1572 Kg/h of a concentrated stream are thus obtained, containing 212 Kg/h of $NaNO_3$, which are then sent through lines 14 and 14a to the electrochemical regeneration section EDMB.

The EDMB electrochemical regeneration section consisted of several set of 10 basic elements in sequence, comprising a cationic membrane RALEX® CM(H), an anionic membrane PC Acid 60 (produced by PCA GmbH) and a bipolar membrane BP-1 (by OSMO), sufficient to process the stream from line 14a. The EDBM section was fed with two pure water streams of 791 Kg/h each, for the regeneration of respectively the acid and alcaline solutions, and produced the following regenerated streams:

- 963 Kg/h of an acid aqueous solution containing 94 Kg/h of nitric acid, which is sent to the scrubber S through lines 16, 16a and 5a;
- 928 Kg/h of a base aqueous solution containing 60 Kg/h of NaOH, which is sent to the ammonia stripping unit ST through lines 15 and 15a;
- 1261 Kg/h of a dilute aqueous solution containing 85 Kg/h of $NaNO_3$, which is preconcentrated by reverse osmosis in the concentration section IO3 to separate 412 Kg/h of pure water (line 20), and sent through lines 19 and 19a, to the section IO2 for further concentration.

27 Kg/h of water were also hydrolized in the process, to produce hydrogen and oxygen that were vented out.

The calculated energy consumption of the EDMB section was around 420 $KJ/mol_{NH3}$ corresponding to 24,700 KJ/tonne of produced urea.

The invention claimed is:

1. A process for the recovery of ammonia contained in a gaseous purging stream produced in a synthesis process of urea, said process comprising the following phases:

a) subjecting the gaseous purging stream to a washing with an aqueous acid solution, at a pH ranging from 1 to 6, with the formation of a first purified gaseous stream and an aqueous solution containing an ammonium salt;

b) subjecting the aqueous solution containing the ammonium salt coming from phase a) to stripping, after treatment with a strong base, at a temperature ranging from 50 to 250° C. and a pressure ranging from 1 to 40 absolute bar, with the formation of a second gaseous stream comprising $NH_3$, $H_2O$ and possibly $CO_2$ and a solution containing a salt of the cation of said strong base;

c) subjecting the solution containing the salt of the cation of the strong base coming from phase b) to a Membrane Electrochemical Process (MEP) with the formation of an aqueous solution of the acid used in phase a), an aqueous solution of the base used in phase b) and possibly a diluted aqueous solution of the cation salt of the strong base;

d) recycling said aqueous solution of the acid and aqueous solution of the base to phase a) and to phase b) respectively, and recycling said second gaseous stream coming from phase b) to the urea synthesis process.

2. The process according to claim 1, characterized in that said gaseous purging stream comes from a solidification section.

3. The process according to claim 1, characterized in that said gaseous purging stream consists of air contaminated by ammonia (about 50÷250 mg/$Nm^3$ air), urea (about 20÷200 mg/$Nm^3$ air) and traces of formaldehyde.

4. The process according to claim 1, characterized in that the gaseous purging stream is at a temperature of about 45-100° C. and is subjected to a preliminary water washing to eliminate most of the urea and formaldehyde present.

5. The process according to claim 1, characterized in that phase a) is carried out with an acid aqueous solution of any strong acid of the protic type.

6. The process according to claim 1, characterized in that phase a) is carried out at a pH ranging from 4 to 5.5.

7. The process according to claim 1, characterized in that the aqueous solution containing the ammonium salt coming from phase a) has a concentration of ammonium salt ranging from 5 to 50% by weight.

8. The process according to claim 1, characterized in that the aqueous solution containing the ammonium salt coming from phase a) is concentrated by means of reverse osmosis before being subjected to phase b).

9. The process according to claim 7, characterized in that the aqueous solution containing the ammonium salt has a concentration of ammonium salt varying from 6 to 66% by weight.

10. The process according to claim 1, characterized in that said first purified gaseous stream which is formed in phase a) is released into the atmosphere.

11. The process according to claim 1, characterized in that said first purified first gaseous stream consists of air or another inert gas having an ammonia content ranging from 10 to 25 mg/$Nm^3$ air and a urea content ranging from 5 to 30 mg/$Nm^3$ air.

12. The process according to claim 1, characterized in that, in phase b), the strong base is an ionic hydroxide with a high solubility in water.

13. The process according to claim 1, characterized in that, in phase b), the strong base is NaOH.

14. The process according to claim 1, characterized in that the aqueous solution of the base is added in such a quantity as to neutralize the ammonium salt solution from the excess acid and substantially remove all of the ammonia.

15. The process according to claim 1, characterized in that said second gaseous stream comprising $NH_3$, $H_2O$ and possibly $CO_2$, which is formed in phase b), is recycled to the synthesis process of urea or a synthesis process of ammonia.

16. The process according to claim 14, wherein said second gaseous stream is subjected to concentration and possible partial or total condensation, before being recycled or sent to other processes.

17. The process according to any of the previous claim 15 or 16, characterized in that said second gaseous stream, as such or in a concentrated form, is recycled to the synthesis process of urea.

18. The process according to claim 1, characterized in that phase b) is carried out by adding steam or by means of indirect heating.

19. The process according to claim 1, characterized in that phase b) is carried out at a temperature ranging from 140 to 200° C. and a pressure ranging from 3 to 18 absolute bar.

20. The process according to claim 1, characterized in that the stripping phase b) is carried out at about 3 bar and at a temperature of about 150° C., the stream comprising $NH_3$, $H_2O$ and $CO_2$ having a concentration of ammonia varying from 15 to 25% by weight.

21. The process according to claim 1, characterized in that the aqueous solution containing the salt of the cation of the strong base coming from phase b), is previously concentrated by reverse osmosis, before being subjected to phase c).

22. The process according to claim 1, characterized in that said aqueous solution of the acid and said aqueous solution of the base which are formed in phase c), independently have a normal concentration of acid and base, respectively, ranging from 0.1N to 5N.

23. The process according to claim 22, where said aqueous solutions of acid and base obtained in phase c) independently have concentrations ranging from 0.5N to 2.5N.

24. The process according to claim 1, characterized in that the aqueous solution of the acid coming from phase c) is used for separating further ammonia from the gaseous purging stream in phase a), after the possible addition of the necessary quantity of water and make-up acid.

25. The process according to claim 1, characterized in that the aqueous solution of the base coming from phase c) is recycled to the stripping phase b), after the possible addition of the necessary quantity of water and make-up base.

26. The process according to claim 1, characterized in that, when in phase c) there is the formation of a diluted aqueous solution of the salt of the cation of the strong base, in the subsequent phase d) said solution is concentrated and then recycled to the feeding to phase c).

27. The process according to claim 1, characterized in that the diluted aqueous solution of the salt is concentrated by means of reverse osmosis and recycled to the feeding to phase c).

28. The process according to claim 1, characterized in that phase a) is effected using nitric acid and phase b) using NaOH, the aqueous solution coming from phase b) being an aqueous solution of $NaNO_3$, with a concentration of $NaNO_3$ varying from 1 to 30% by weight.

29. The process according to claim 1, characterized in that the Membrane Electrochemical Process (MEP) which forms phase c) is an Electrodialysis process (ED).

30. Equipment for effecting the process according to claim 1, characterized in that it comprises:

an acid scrubber unit where a gaseous ammonia stream is put in contact with an acid, an ammonia stripping unit, where an aqueous stream of an ammonium salt is put in contact with a strong base and the free ammonia thus produced is extracted as vapour from the aqueous stream and a Bipolar Membrane Electrodialysis (EDMB) or Electrodialysis (ED) unit where a stream containing the acid, a stream containing the base and possibly a stream containing a diluted solution of the corresponding salt are formed.

* * * * *